US008183285B2

(12) United States Patent
Terauchi et al.

(10) Patent No.: US 8,183,285 B2
(45) Date of Patent: May 22, 2012

(54) THERAPEUTIC AGENT FOR IRRITABLE BOWEL SYNDROME AND METHODS THEREOF

(75) Inventors: Jun Terauchi, Osaka (JP); Fumihiko Sato, Osaka (JP); Nobuhiro Inatomi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/826,473

(22) Filed: Jun. 29, 2010

(65) Prior Publication Data

US 2010/0267821 A1 Oct. 21, 2010

Related U.S. Application Data

(63) Continuation of application No. 12/225,269, filed as application No. PCT/JP2007/055526 on Mar. 19, 2007, now abandoned.

(30) Foreign Application Priority Data

Mar. 20, 2006 (JP) .................................. 2006-076532

(51) Int. Cl.
*A61K 31/343* (2006.01)
(52) U.S. Cl. ...................................................... 514/468
(58) Field of Classification Search ........................ None
See application file for complete search history.

(56) References Cited

U.S. PATENT DOCUMENTS

| 5,633,276 | A | 5/1997 | North et al. | |
| 6,034,239 | A | 3/2000 | Ohkawa et al. | |
| 6,218,429 | B1 | 4/2001 | Ohkawa et al. | |
| 6,348,485 | B1 * | 2/2002 | Ohkawa et al. | 514/394 |
| 2005/0203130 | A1 * | 9/2005 | Buntinx | 514/316 |
| 2007/0088079 | A1 * | 4/2007 | Hirai et al. | 514/468 |

FOREIGN PATENT DOCUMENTS

| EP | 1 064 941 A1 | 1/2001 |
| JP | 10-287665 | 10/1998 |
| JP | 2001-026539 | 1/2001 |
| JP | 2002-226367 | 8/2002 |
| WO | WO 97/32871 A1 | 9/1997 |
| WO | WO-2007/034778 | 3/2007 |

OTHER PUBLICATIONS

The Merck Manual, 17th edition, (1999), p. 312.*
M. Jarrett, RN, Phd, et al., "Sleep Disturbance Influences Gastrointestinal Symptoms in Women with Irritable Bowel Syndrome", *Digestive Diseases and Sciences*, 45(5), pp. 952-959 (May 2000).
W.Z. Lu et al., "Melatonin improves bowel symptons in female patients with irritable bowel syndrome: a double-blind placebo-controlled study", *Ailment Pharmacol Ther*, vol. 22, pp. 927-934 (2005).
J. J.T. Robert, Ph.D., et al., "Modulation of Sleep Quality and Autonomic Functioning by Symptoms of Depression in Women with Irritable Bowel Syndrome", *Digestive Diseases and Sciences*, 49(7/8), pp. 1250-1258 (Aug. 2004).
G.H. Song et al., "Melatonin attenuates stress-induced defecation: lesson from a rat model of stress-induced gut dysfunction", *Neurogastroenterol Motil*, vol. 17, pp. 744-750 (2005).
Uchikawa O et al: "Synthesis of a novel series of tricyclic indan derivatives as melatonin receptor agonists", Journal of Medicinal Chemistry, Jan. 1, 2002, pp. 4222-4239, vol. 45, American Chemical Society, US.
Kobayashi S, Ikeda K, Suzuki M, Yamada T, Miyata K. "Effects of YM905, a novel muscarinic M3-receptor antagonist, on experimental models of bowel dysfunction in vivo".*Jpn J Pharmacol*. 86(3):281-8 (Jul. 2001;).
Okano S, Nagaya H, Ikeura Y, Natsugari H, Inatomi N. "Effects of TAK-637, a novel neurokinin-1 receptor antagonist, on colonic function in vivo". *J Pharmacol Exp Ther*.;298(2):559-64 (Aug. 2001).
Okano S, Ikeura Y, Inatomi N. "Effects of tachykinin NK1 receptor antagonists on the viscerosensory response caused by colorectal distention in rabbits". *J Pharmacol Exp Ther*. ;300(3):925-31 (Mar. 2002).
La JH, Kim TW, Sung TS, Kang JW, Kim HJ, Yang IS. "Visceral hypersensitivity and altered colonic motility after subsidence of inflammation in a rat model of colitis", World J Gastroenterol. 9(12):2791-5; (Dec. 2003).

* cited by examiner

*Primary Examiner* — Phyllis G. Spivack
(74) *Attorney, Agent, or Firm* — Edwards Wildman Palmer LLP; David G. Conlin; Amy DeCloux (57) ABSTRACT

The present invention provides a therapeutic agent and methods thereof for the treatment for irritable bowel syndrome. The agent comprises a compound represented by formula (I):

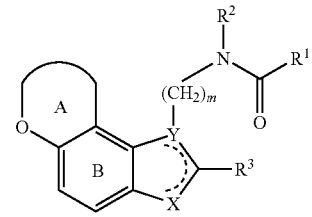

wherein, $R^1$ represents an optionally substituted hydrocarbon group, etc., $R^2$ represents a hydrogen atom or an optionally substituted hydrocarbon group, $R^3$ represents a hydrogen atom, an optionally substituted hydrocarbon group, etc., X represents $CHR^4$, $NR^4$, CO, O or S (wherein, $R^4$ represents a hydrogen atom, an optionally substituted hydrocarbon group, etc.), Y represents C, CH or N, represents a single bond or double bond, ring A represents an optionally substituted 5- to 7-membered oxygen-containing heterocyclic ring, ring B represents an optionally substituted benzene ring, and m represents an integer of 1 to 4, or a salt thereof, wherein the compound represented by formula (I) or a salt thereof is (S)—N-[2-(1,6,7,8-tetrahydro-2H-indeno[5,4-b]furan-8-yl)ethyl]propionamide.

1 Claim, 4 Drawing Sheets

THERAPEUTIC AGENT FOR IRRITABLE BOWEL SYNDROME AND METHODS THEREOF

RELATED APPLICATIONS

This application is a continuation of U.S. patent application Ser. No. 12/225,269 filed on Sep. 17, 2008, which claims priority to PCT/JP2007/055526, filed on Mar. 19, 2007, which claims the benefit of JP 2006-076532, filed Mar. 20, 2006. The contents of each of these applications is incorporated herein by reference in their entirety.

TECHNICAL FIELD

The present invention relates to a prophylactic or therapeutic agent for irritable bowel syndrome.

BACKGROUND ART

Irritable bowel syndrome (IBS) is a disorder that shows dysfunction of lower bowel such as abnormal defecation (diarrhea or constipation) and concomitant abdominal symptoms of abdominal pain and discomfort lasting for several months.

The pathophysiology of irritable bowel syndrome is still unclear, but it is now that mental stress is closely involved in the development of symptom, and a high coincidence rate of mental disorder such as depression and hysteria has been made known. Sleep disorder is often observed in patients with irritable bowel syndrome, and it is reported recently that sleep disorder in patients with irritable bowel syndrome correlates with the degree of abdominal symptoms (see non-patent documents 1.

In addition, there is a report that, compared to healthy individuals and patients with irritable bowel syndrome having no depressive symptoms, patients with irritable bowel syndrome having depressive symptoms show more severe abdominal symptoms and sleep disorders (see non-patent document 2).

Further, there is a report that melatonin, known as a hormone regulating sleep-wake cycle, improves significantly the abdominal symptoms such as abdominal pain, abdominal bloating and sense of urgency for defecation in female patients suffering from irritable bowel syndrome (see non-patent document 3).

Furthermore, there is a report that melatonin shows an inhibitory action on partial restraint stress-induced defecation which is an experimental model based on defecation abnormality for irritable bowel syndrome (see non-patent document 4).

In addition, patent document 1 discloses that (S)—N-[2-(1,6,7,8-tetrahydro-2H-indeno[5,4-b]furan-8-yl)ethyl]propionamide (general name: Ramelteon) has a melatonin receptor MT1/MT2 agonistic action.

[patent document 1] U.S. Pat. No. 6,034,239
[non-patent document 1] Monica Jarrett et. al., Digestive Diseases and Sciences, Vol. 45, No. 5 (May 2000), pp. 952-959
[non-patent document 2] Jennifer J. T. Robert et. al., Digestive Diseases and Sciences, Vol. 49, Nos. 7/8 (August 2004), pp. 1250-1258
[non-patent document 3] W. Z. Lu et. al., Aliment Pharmacol Ther 2005; 22: pp. 927-934
[non-patent document 4] G. S. Song et. al., Neurogastroenterol Motil 2005; 17: pp. 744-750

DISCLOSURE OF INVENTION

Problems to be Solved by the Invention

The object of the present invention is to provide a prophylactic or therapeutic agent for irritable bowel syndrome.

Means of Solving the Problems

The present inventors found out that certain melatonin agonists are effective for a prevention or treatment of irritable bowel syndrome, and resulted in the completion of the present invention.

That is, the present invention provides:

[1] A pharmaceutical composition for a prevention or treatment of irritable bowel syndrome, which comprises a compound represented by formula (I):

wherein, $R^1$ represents an optionally substituted hydrocarbon group, an optionally substituted amino group or an optionally substituted heterocyclic group, $R^2$ represents a hydrogen atom or an optionally substituted hydrocarbon group, $R^3$ represents a hydrogen atom, an optionally substituted hydrocarbon group or an optionally substituted heterocyclic group, X represents $CHR^4$, $NR^4$, CO, O or S (wherein, $R^4$ represents a hydrogen atom, an optionally substituted hydrocarbon group or hydroxyl group), Y represents C, CH or N,
----- represents a single bond or double bond,
ring A represents an optionally substituted 5- to 7-membered heterocyclic ring containing, an oxygen atom,
ring B represents an optionally substituted benzene ring, and m represents an integer of 1 to 4, or a salt thereof;

[2] The pharmaceutical composition for a prevention or treatment of irritable bowel syndrome according to the above-mentioned [1], wherein the compound represented by formula (I) or a salt thereof is (S)—N-[2-(1,6,7,8-tetrahydro-2H-indeno[5,4-b]furan-8-yl)ethyl]propionamide;

[3] A method for a prevention or treatment of irritable bowel syndrome, which comprises administering an effective amount of a compound represented by formula (I):

wherein, $R^1$ represents an optionally substituted hydrocarbon group, an optionally substituted amino group or an optionally substituted heterocyclic group, $R^2$ represents a hydrogen atom or an optionally substituted hydrocarbon group, $R^3$ represents a hydrogen atom, an optionally substituted hydrocarbon group or an optionally substituted heterocyclic group, X represents $CHR^4$, $NR^4$, CO, O or S (wherein, $R^4$ represents a hydrogen atom, an optionally substituted hydrocarbon group or hydroxyl group), Y represents C, CH or N,

----- represents a single bond or double bond, ring A represents an optionally substituted 5- to 7-membered heterocyclic ring containing an oxygen atom, ring B represents an optionally substituted benzene ring, and m represents an integer of 1 to 4, or a salt thereof;

[4] The method for a prevention or treatment according to the above-mentioned [3], wherein the compound represented by formula (I) or a salt thereof is (S)—N-[2-(1,6,7,8-tetrahydro-2H-indeno[5,4-b]furan-8-yl)ethyl]propionamide;

[5] Use of a compound represented by formula (I):

wherein, $R^1$ represents an optionally substituted hydrocarbon group, an optionally substituted amino group or an optionally substituted heterocyclic group, $R^2$ represents a hydrogen atom or an optionally substituted hydrocarbon group, $R^3$ represents a hydrogen atom, an optionally substituted hydrocarbon group or an optionally substituted heterocyclic group, X represents $CHR^1$, $NR^4$, CO, O or S (wherein, $R^4$ represents a hydrogen atom, an optionally substituted hydrocarbon group or hydroxyl group), Y represents C, CH or N, ----- represents a single bond or double bond, ring A represents an optionally substituted 5- to 7-membered heterocyclic ring containing an oxygen atom, ring B represents an optionally substituted benzene ring, and m represents an integer of 1 to 4, or a salt thereof, for the manufacture of a pharmaceutical composition for a prevention or treatment of irritable bowel syndrome;

[6] The use according to the above-mentioned (5), wherein the compound represented by formula (I) or a salt thereof is (S)—N-[2-(1,6,7,8-tetrahydro-2H-indeno[5,4-b]furan-8-yl) ethyl]propionamide; and the like.

BEST MODE FOR CARRYING OUT THE INVENTION

Examples of melatonin agonists to be used for a preventive or therapeutic agent for irritable bowel syndrome in the present invention include a compound represented by the above formula (I) or a salt thereof, VEC-162 (Vanda), LY-156735 (Lilly), Agomelatine (Servier), and the like.

Among them, the compound represented by the above formula (I) or a salt thereof is preferred.

Hereinafter, the compound represented by formula (I) or a salt thereof will be illustrated.

In the above formula (I), $R^1$ represents an optionally substituted hydrocarbon group, an optionally substituted amino group or an optionally substituted heterocyclic group, $R^2$ represents a hydrogen atom or an optionally substituted hydrocarbon group, $R^3$ represents a hydrogen atom, an optionally substituted hydrocarbon group or an optionally substituted heterocyclic group, X represents $CHR^4$; $NR^4$, CO, O or S (wherein, $R^4$ represents a hydrogen atom, an optionally substituted hydrocarbon group or hydroxyl group), Y represents C, CH or N, ----- represents a single bond or double bond, ring A represents an optionally substituted 5- to 7-membered heterocyclic ring containing an oxygen atom, ring B represents an optionally substituted benzene ring, and m represents an integer of 1 to 4.

Preferably, in case that X represents $CH_2$, Y is C or CH.

In this specification, examples of the "hydrocarbon group" in the "optionally substituted hydrocarbon group" include an aliphatic hydrocarbon group, a monocyclic saturated hydrocarbon group and an aromatic hydrocarbon group, and preferred is a group having 1 to 16 carbons. Specifically, for example, an alkyl group, an alkenyl group, and an alkynyl group, a cycloalkyl group and aryl group are used.

As the "alkyl group", for example, a lower alkyl group and the like are preferred, and a $C_{1-6}$ alkyl group such as methyl, ethyl, propyl, isopropyl, butyl, isobutyl, sec-butyl, tert-butyl, pentyl and hexyl is used generally.

As the "alkenyl group", for example, a lower alkenyl group and the like are preferred, and a $C_{2-6}$ alkenyl group such as vinyl, 1-propenyl, allyl, isopropenyl, butenyl and isobutenyl is used generally.

As the "alkynyl group", for example, a lower alkynyl group and the like are preferred, and a $C_{2-6}$ alkynyl group such as ethynyl, propargyl and 1-propynyl is used generally.

As the "cycloalkyl group", for example, a lower cycloalkyl group and the like are preferred, and a $C_{3-6}$ cycloalkyl group such as cyclopropyl, cyclobutyl, cyclopentyl and cyclohexyl is used generally.

As the "aryl group", for example, a $C_{6-14}$ aryl group such as phenyl, 1-naphthyl, 2-naphthyl, biphenylyl, 2-anthryl and the like are preferred, and for example, phenyl group is used generally.

Examples of the substituent which the "hydrocarbon group" of the "optionally substituted hydrocarbon group" may have, include a halogen atom (e.g., fluorine, chlorine, bromine, iodine), nitro, cyano, hydroxyl, an optionally halogenated lower alkyl group (e.g., an optionally halogenated $C_{1-6}$ alkyl group such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), a lower alkoxy group (e.g., C-alkoxy group such as methoxy, ethoxy, propoxy, isopropoxy, butoxy, isobutoxy, pentyloxy, hexyloxy, etc.), amino group, a mono-lower alkylamino group (e.g., mono-$C_{1-6}$ alkylamino group such as methylamino, ethylamino, etc.), a di-lower alkylamino group (e.g., di-$C_{1-6}$ alkylamino group such as dimethylamino, diethylamino etc.), a carboxyl group, a lower alkylcarbonyl group (e.g., $C_{1-6}$ alkylcarbonyl group such as acetyl, propionyl, etc.), a lower alkoxycarbonyl group (e.g., $C_{1-6}$ alkoxy-carbonyl group such as methoxycarbonyl, ethoxycarbonyl, propoxycarbonyl, butoxycarbonyl etc.), a carbamoyl group, a mono-lower alkylcarbamoyl group (e.g., mono-$C_{1-6}$ alkyl-carbamoyl group such as methylcarbamoyl, ethylcarbamoyl, etc.), a di-lower alkylcarbamoyl group (e.g., di-$C_{1-6}$ alkyl-carbamoyl group such as dimethylcarbamoyl, diethylcarbamoyl, etc.), an arylcarbamoyl group (e.g., $C_{6-10}$ aryl-carbamoyl group such as phenylcarbamoyl, naphthylcarbamoyl, etc.), an aryl group (e.g., $C_{6-10}$ aryl group such as phenyl, naphthyl, etc.), an aryloxy group (e.g., $C_{6-10}$ aryloxy group such as phenyloxy, naphthyloxy, etc.), an optionally halogenated lower alkylcarbonylamino group (e.g., an optionally halogenated alkyl-carbonylamino group such as acetylamino, trifluoroacetylamino, etc.), oxo group, and the like. The "hydrocarbon group" of the "optionally substituted hydrocarbon group" may have 1 to 5, preferably 1 to 3 of the above substituents at substitutable positions of the hydrocarbon group, and when the number of the substituents is 2 or more, the respective substituents may be the same or different.

In this specification, examples of the "heterocyclic group" of the "optionally substituted heterocyclic group" include a 5- to 14-membered (preferably 5- to 10-membered) (monocyclic to tricyclic, preferably monocyclic or bicyclic) heterocyclic group containing one or two kinds of to 4 (preferably 1 to 3) heteroatoms selected from a nitrogen atom, an oxygen atom and a sulfur atom in addition to carbon atoms. For example, 5-membered ring group containing 1 to 4 hetero atoms selected from an oxygen atom, a sulfur atom and a nitrogen atom in addition to carbon atoms, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isooxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1-, 2- or 3-triazolyl, 1-, 2- or 4-triazolyl, 1H- or 2H-tetrazolyl, and the like, 6-membered ring group containing 1 to 4 hetero atoms selected from an oxygen atom, a sulfur atom and a nitrogen atom in addition to carbon atoms, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, piperazinyl, triazinyl, 3- or 4-pyridazinyl, pyrazinyl, N-oxido-3- or 4-pyridazinyl, and the like, and a bicyclic or tricyclic fused ring group containing 1 to 4 hetero atoms selected from an oxygen atom, a sulfur atom and a nitrogen atom in addition to carbon atoms (preferably, a group formed by condensing the above-mentioned 5- or 6-membered ring with one or two of 5- or 6-membered ring group optionally containing 1 to 4 hetero atoms selected from an oxygen atom, a sulfur atom and a nitrogen atom in addition to carbon atoms), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl, and the like are used. Among them, a 5- to 7-membered (preferably 5- or 6-membered) heterocyclic group containing 1 to 3 heteroatoms selected from a nitrogen atom, an oxygen atom and a sulfur atom in addition to carbon atoms is preferred.

Examples of the substituent which the "heterocyclic group" of the "optionally substituted heterocyclic group" may have, include a halogen atom (e.g., fluorine, chlorine, bromine, iodine), a lower alkyl group (e.g., $C_{1-6}$ alkyl group such as methyl, ethyl, propyl, isopropyl, butyl, isobutyl, sec-butyl, tert-butyl, pentyl, hexyl, etc.), a cycloalkyl group (e.g., $C_{3-6}$ cycloalkyl group such as cyclopropyl, cyclobutyl, cyclopentyl, cyclohexyl, etc.), a lower alkynyl group (e.g., $C_{2-6}$ alkynyl group such as ethynyl, 1-propynyl, propargyl, etc.), a lower alkenyl group (e.g., $C_{2-6}$ alkenyl group such as vinyl, allyl, isopropenyl, butenyl, isobutenyl, etc.), an aralkyl group (e.g., $C_{7-11}$ aralkyl group such as benzyl, α-methylbenzyl, phenethyl, etc.), an aryl group (e.g., $C_{6-10}$ aryl group such as phenyl, naphthyl, etc., preferably phenyl group), a lower alkoxy group (e.g., $C_{1-6}$ alkoxy group such as methoxy, ethoxy, propoxy, isopropoxy, butoxy, isobutoxy, sec-butoxy, ter-butoxy, etc.), an aryloxy group (e.g., $C_{6-10}$ aryloxy group such as phenoxy, etc.), a lower alkanoyl group (e.g., $C_{1-6}$ alkyl-carbonyl group such as formyl, acetyl, propionyl, butyryl, isobutyryl, etc.), an arylcarbonyl (e.g., $C_{6-10}$ arylcarbonyl group such as benzoyl group, naphthoyl group, etc.), a lower alkanoyloxy group (e.g., $C_{1-6}$ alkyl-carbonyloxy group such as formyloxy, acetyloxy, propionyloxy, butyryloxy, isobutyryloxy, etc.), an arylcarbonyloxy $C_{6-10}$ aryl-carbonyloxy group such as benzoyloxy, naphthoyloxy, etc.), a carboxyl group, a lower alkoxycarbonyl group (e.g., $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxycarbonyl group (e.g., $C_{7-11}$ aralkyloxycarbonyl group such as benzyloxycarbonyl, etc.), a carbamoyl group; a mono-, di- or tri-halogeno-lower alkyl group (e.g., mono-, di- or tri-halogeno-$C_{1-4}$ alkyl group such as chloromethyl, dichloromethyl, trifluoromethyl, 2,2,2-trifluoroethyl, etc.), oxo group, amidino group, imino group, amino group, a mono-lower alkylamino group (e.g., mono-$C_{1-4}$ alkylamino group such as methylamino, ethylamino, propylamino, isopropylamino, butylamino, etc.), a di-lower alkylamino group (e.g., di-$C_{1-4}$ alkylamino group such as dimethylamino, diethylamino, dipropylamino, diisopropylamino, dibutylamino, methylethylamino, etc.), a 3- to 6-membered cyclic amino group optionally containing 1 to 3 heteroatoms selected from an oxygen atom, a sulfur atom and a nitrogen atom in addition to carbon atom and one nitrogen atom (e.g., 3- to 6-membered cyclic amino group such as aziridinyl, azetidinyl, pyrrolidinyl, pyrrolinyl, pyrrolyl, imidazolyl, pyrazolyl, imidazolidinyl, piperidinyl, morpholinyl, dihydropyridyl, pyridyl, N-methylpiperazinyl, N-ethylpiperazinyl, etc.), alkylene dioxy group (e.g., $C_{1-3}$ alkylene dioxy group such as methylene dioxy, ethylene dioxy, etc.), hydroxyl group, nitro group, cyano group, mecapto group, sulfo group, sulfino group, phosphono group, sulfamoyl group, mono-alkylsulfamoyl group (e.g., mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), di-alkylsulfamoyl group (e.g., di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., $C_{1-6}$ alkylthio group such as methylthio, ethylthio, propylthio, isopropylthio, butylthio, sec-butylthio, tert-butylthio, etc.), an arylthio group (e.g., $C_{6-10}$ arylthio group such as phenylthio, naphthylthio, etc.), a lower alkylsulfinyl group (e.g. $C_{1-6}$ alkylsulfinyl group such as methylsulfinyl, ethylsulfinyl, propylsulfinyl, butylsulfinyl, etc.), an arylsulfinyl group (e.g., $C_{6-10}$ arylsulfinyl group such as phenylsulfinyl, naphthylsulfinyl, etc.), a lower alkylsulfonyl group (e.g. $C_{1-6}$ alkylsulfonyl group such as methylsulfonyl; ethylsulfonyl, propylsulfonyl, butylsulfonyl, etc.), an arylsulfonyl group (e.g., $C_{6-10}$ arylsulfonyl group such as phenylsulfonyl, naphthylsulfonyl, etc.), and the like.

The "heterocyclic group" of the "optionally substituted heterocyclic group" may have 1 to 5, preferably 1 to 3 of the above substituents at substitutable positions of the heterocyclic group, and when the number of the substituents is 2 or more, the respective substituents may be the same or different.

In the present specification, the "optionally substituted amino group" includes an amino group that may have one or two of the above-mentioned "optionally substituted hydrocarbon group" and the like as a substituent. As a preferred substituent that the "amino group" may have, for example, an optionally substituted $C_{1-6}$ alkyl group and an optionally substituted $C_{6-10}$ aryl group are exemplified. As the substituent that the "$C_{1-6}$ alkyl group" and "$C_{6-10}$ aryl group" may have, substituents similar to those that may be possessed by the above-mentioned "hydrocarbon group" are used.

In the present specification, the "lower alkyl group" of the "optionally substituted lower alkyl group" indicates $C_{1-6}$ alkyl group such as methyl, ethyl, propyl, isopropyl, butyl, isobutyl, sec-butyl and tert-butyl, and may have 1 to 3 of the substituents that may be possessed by the above-mentioned "hydrocarbon group", as a substituent.

In the present specification, the "lower alkoxy group" of the "optionally substituted lower alkoxy group" indicates a $C_{1-6}$ alkoxy group such as methoxy, ethoxy, propoxy, isopropoxy, butoxy, isobutoxy, sec-butoxy and tert-butoxy, and may have 1 to 3 of the substituents that may be possessed by the above-mentioned "hydrocarbon group", as a substituent.

In the present specification, the "optionally substituted benzene ring" indicates a benzene ring that may have one or two substituents selected from a halogen atom (e.g., fluorine, chlorine, bromine, iodine), an optionally substituted hydrocarbon group, an optionally substituted amino group, an amido group (e.g., $C_1$-3 acylamino group such as formamide, acetamide, etc.), hydroxy group, an optionally substituted lower alkoxy group and lower alkylene dioxy group (e.g., $C_{1-3}$ alkylene dioxy group such as methylene dioxy, ethylene dioxy, etc.), at substitutable positions.

As these "optionally substituted hydrocarbon group", "optionally substituted amino group" and "optionally substituted lower alkoxy group", for example, groups similar to those detailed above are used. When the number of the substituents that these "hydrocarbon group", "amino group" and "lower alkoxy group" may have is 2 or more, the respective substituents may be the same or different.

Preferred examples of the "optionally substituted benzene ring" include a benzene ring that may be substituted with one or two substituents selected from a halogen atom (e.g., fluorine, chlorine), a $C_{1-6}$ alkyl (e.g., methyl, ethyl, etc.); hydroxy group and mono-$C_{1-6}$ alkylamino group.

In the above-mentioned formula (I), $R^1$ represents an optionally substituted hydrocarbon group, an optionally substituted amino group or optionally substituted heterocyclic group.

Preferred examples of the "hydrocarbon group" in the "optionally substituted hydrocarbon group" include an alkyl group (e.g., $C_{1-6}$ alkyl group such as methyl, ethyl, propyl, isopropyl, etc.), an alkenyl group (e.g., $C_{2-6}$ alkenyl group such as vinyl, etc.), an alkynyl group (e.g., $C_{2-6}$ alkynyl group such as ethynyl, etc.), a cycloalkyl group (e.g., $C_{3-6}$ cycloalkyl group such as cyclopropyl, cyclobutyl, cyclopentyl, cyclohexyl, etc.), and aryl group (e.g., $C_{6-14}$ aryl group such as phenyl, etc.), and in particular, an alkyl group (e.g., $C_{1-6}$ alkyl group such as methyl, etc.) and a cycloalkyl group (e.g., $C_{3-6}$ cycloalkyl group such as cyclopropyl, etc.) are used widely. The "alkyl group", "alkenyl group", "alkynyl group", "cycloalkyl group" and "aryl group" may have 1 to 5, preferably, 1 to 3, substituents such as those that the above-mentioned "hydrocarbon group" may have, preferably, halogen atom such as fluorine, etc.

As the preferred substituent of the "optionally substituted amino group" represented by $R^1$, for example, one or two of an optionally substituted lower alkyl group, an optionally substituted aryl group and the like are used, in particular, one of the optionally substituted lower alkyl group and the like is used. As the "lower alkyl group", for example, $C_6$ alkyl such as methyl, ethyl, propyl, isopropyl, butyl, isobutyl, sec-butyl and tert-butyl is used. The "lower alkyl group" may have 1 to 3 substituents that may be possessed by, for example, the above-mentioned "hydrocarbon group". As the "aryl group", for example, $C_{6-10}$ aryl group such as phenyl group and the like is used. The "aryl group" may have 1 to 5, preferably 1 to 3, substituents such as those that the above-mentioned "hydrocarbon group" may have, preferably, halogen atom such as fluorine, chlorine, etc., $C_{1-6}$ alkoxy group such as methoxy, ethoxy, etc. As the "optionally substituted amino group", for example, phenyl amino group substituted with 1 to 3 lower alkoxys (e.g., $C_{1-4}$ alkoxy group such as methoxy, etc.) or mono-alkylamino group substituted with lower alkyl group (e.g., $C_{1-4}$ alkyl group such as methyl, ethyl, propyl, butyl and tert-butyl) is used widely.

As the preferred "heterocyclic group" of the "optionally substituted heterocyclic group" represented by $R^1$, for example, 5- or 6-membered heterocyclic group containing 1 to 3 heteroatoms selected from a nitrogen atom, an oxygen atom and a sulfur atom in addition to carbon atoms is used. Specifically, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2-furyl or 3-furyl, pyrazinyl, 2-pyrimidinyl, 3-pyrrolyl, 3-pyridazinyl, 3-isothiazolyl, 3-isooxazolyl, and the like are exemplified. A 6-membered nitrogen containing-heterocyclic group (e.g., pyridyl, etc.) and the like are particularly preferably used.

As the preferred substituent of the "optionally substituted heterocyclic group", for example, a halogen atom (e.g., chlorine, fluorine, etc.), a $C_{1-6}$ alkyl group (e.g., methyl, ethyl, etc.), alkoxy group (e.g., methoxy, ethoxy, etc.), aralkyloxycarbonyl group (e.g., $C_{7-12}$ aralkyloxy-carbonyl such as benzyloxycarbonyl), and the like are used.

$R^1$ is preferably, for example, (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group or (vii) an optionally substituted 5- or 6-membered nitrogen containing-heterocyclic group.

Preferred examples of the above-mentioned "lower alkyl group" are $C_{1-6}$ alkyl group such as methyl, ethyl, propyl, isopropyl, butyl, pentyl and hexyl, and the like. Preferred examples of the "lower cycloalkyl group" are $C_{3-6}$ cycloalkyl such as cyclopropyl, cyclobutyl, cyclopentyl and cyclohexyl, and the like. Preferred examples of the "lower alkenyl group" are $C_{2-6}$ alkenyl group such as vinyl, 1-propenyl, butenyl, and the like. Preferred examples of the "aryl group" are $C_{6-10}$ aryl group such as phenyl, 1-naphthyl, 2-naphthyl, and the like. Preferred examples of the "lower alkylamino group" are mono- or di-$C_{1-6}$ alkylamino group such as methylamino, ethylamino, propylamino, isopropylamino, butylamino, tert-butylamino, dimethylamino, diethylamino, methylethylamino, and the like. Preferred examples of the "arylamino group" are $C_{6-10}$ arylamino group such as phenylamino, and the like. Preferred examples of the "5- or 6-membered nitrogen containing-heterocyclic group" are a 5- or 6-membered nitrogen containing-heterocyclic group such as 2-, 3- or 4-pyridyl, and the like. These groups may each have 1 to 5 substituents such as those the above-mentioned "hydrocarbon group" may have.

In this specification, ---- represents a single bond or double bond.

The more preferred examples of $R^1$ include i) $C_{1-6}$ alkyl group which may be substituted with 1 to 4 of halogen, hydroxy group or $C_{1-6}$ alkoxy group, ii) $C_{3-6}$ cycloalkyl group, iii) $C_{2-6}$ alkenyl group, iv) $C_{6-10}$ aryl group which may be substituted with 1 to 4 of $C_{1-6}$ alkoxy, nitro, halogeno$C_{1-6}$ alkyl-carbonylamino or halogen atom, v) mono- or di-$C_{1-6}$ alkylamino group, vi) $C_{6-10}$ arylamino group which may be substituted with 1 to 3 of $C_{1-6}$ alkoxy or vii) 6-membered nitrogen containing-heterocyclic group which may be substituted with 1 or 2 of $C_{7-11}$ aralkyloxycarbonyl group. In particular, an optionally halogenated $C_{1-6}$ alkyl group (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), $C_{3-6}$ cycloalkyl group (e.g., cyclopropyl, cyclobutyl, cyclopentyl, cyclohexyl, etc.) or mono-$C_{1-6}$ alkylamino group (e.g., methylamino, ethylamino, propylamino, isopropylamino, butylamino, tert-butylamino, etc.) are used widely, and among them, an optionally halogenated $C_{1-6}$ alkyl group or mono-$C_{1-6}$ alkylamino group, particularly an optionally halogenated $C_{1-6}$ alkyl group, inter alia, $C_{1-3}$ alkyl group (e.g., methyl, ethyl, propyl, etc.) is preferred.

In the above formula (I), $R^2$ represents a hydrogen atom or an optionally substituted hydrocarbon group.

As $R^2$, a hydrogen atom or an optionally substituted lower ($C_{1-6}$) alkyl group is preferably used, and more preferably a hydrogen atom or a lower ($C_{1-6}$) alkyl group, in particular, a hydrogen atom is used widely.

In the above formula (I), $R^3$ represents a hydrogen atom, an optionally substituted hydrocarbon group or an optionally substituted heterocyclic group.

As the preferred examples of the "hydrocarbon group" in the "optionally substituted hydrocarbon group" represented by $R^3$, alkyl group (e.g., $C_{1-6}$ alkyl group such as methyl, ethyl, propyl, isopropyl, etc.), alkenyl group (e.g., $C_{2-6}$ alkenyl group such as vinyl, etc.), alkynyl group (e.g., $C_{2-6}$ alkynyl group such as ethynyl, etc.), cycloalkyl group (e.g., $C_{3-6}$ cycloalkyl group such as cyclopropyl, cyclobutyl, cyclopentyl, cyclohexyl, etc.) and aryl group (e.g., $C_{6-14}$ aryl group such as phenyl, etc.), in particular, alkyl group (e.g., $C_{1-6}$ alkyl group such as methyl, etc.) and aryl group (e.g., $C_{6-14}$ aryl group such as phenyl, etc.) are used widely. The "alkyl group", "alkenyl group", "alkynyl group", "cycloalkyl group" and "aryl group" may have 1 to 5, preferably, 1 to 3, substituents such as those that the above-mentioned "hydrocarbon group" may have, preferably, halogen atom such as fluorine atom, etc.

As the preferred examples of the "heterocyclic group" in the "optionally substituted heterocyclic group" represented by $R^3$, a 5- or 6-membered heterocyclic group containing 1 to 3 heteroatoms selected from a nitrogen atom, an oxygen atom and a sulfur atom in, addition to carbon atoms is used. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2-, or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isooxazolyl, and the like are exemplified. A 6-membered nitrogen containing heterocyclic group (e.g., pyridyl, etc.) is used particularly preferably.

As the preferred examples of the substituent of the "optionally substituted heterocyclic group" represented by $R^3$, for example, a halogen atom (e.g., chlorine, fluorine, etc.), a $C_{1-6}$ alkyl (e.g., methyl, ethyl, etc.), a $C_{1-6}$ alkoxy group (e.g., methoxy, ethoxy, etc.), an aralkyloxycarbonyl group (e.g., $C_{7-12}$ aralkyloxy-carbonyl such as benzyloxycarbonyl, etc.), amino group, mono-$C_{1-6}$ alkylamino group (e.g., methylamino, ethylamino, etc.), di-$C_{1-6}$ alkylamino group (e.g., dimethylamino, diethylamino, etc.), and the like are used.

$R^3$ is preferably, for example, (i) a hydrogen atom, (ii) an optionally substituted lower alkyl group, (iii) an optionally substituted aryl group, (iv) an optionally substituted 5- or 6-membered heterocyclic group or the like, furthermore for example, (i) a hydrogen atom, (ii) a lower alkyl group, (iii) an optionally substituted $C_{6-10}$ aryl group, (iv) an optionally substituted 6-membered nitrogen containing heterocyclic group or the like is preferred. Examples of the substituent include a halogen atom, a $C_{1-6}$ alkyl, a $C_{1-6}$ alkoxy group, amino group, mono-$C_{1-6}$ alkylamino group, di-$C_{1-6}$ alkylamino group, and the like. For $R^3$, a hydrogen atom, phenyl group and 2-, 3- or 4-pyridyl group are more preferred. Particularly preferred is a hydrogen atom for $R^3$.

In the above formula (I), X represents $CHR^4$, $NR^4$, CO, O or S (wherein, $R^4$ represents a hydrogen atom, a hydroxyl group or an optionally substituted hydrocarbon group).

Preferred examples of $R^4$ include a hydrogen atom, a hydroxyl group and an optionally substituted lower ($C_{1-6}$) alkyl group, and a hydrogen atom is used widely.

X is preferably $CHR^4$ ($R^4$ has the same meaning as the above-mentioned), CO, O or S. Or X is preferably $CHR^4$ or $NR^4$ ($R^4$ has the same meaning as the above-mentioned).

In the above formula (I), ring A represents an optionally substituted 5- to 7-membered heterocyclic ring containing an oxygen atom.

Examples of the "5- to 7-membered heterocyclic ring containing an oxygen atom" include a 5- to 7-membered (preferably 5- or 6-membered) heterocyclic ring optionally containing 1 to 3 (preferably 1 or 2) of one or two heteroatoms selected from a nitrogen atom, an oxygen atom and a sulfur atom in addition to carbon atoms and an oxygen atom, and the like. As the ring, the ring represented by formula:

wherein, E represents (i) $CH_2CH_2$, (ii) $CH=CH$, (iii) $CH_2O$, (iv) $OCH_2$, (v) $CH_2S(O)_{q'}$ (q' is an integer of 0 to 2), (vi) $S(O)_{q'}CH_2$ (q' is as defined above), (vii) $CH_2NH$, (viii) $NHCH_2$, (ix) N=N, (x) CH=N, (xi) N=CH or (xii) CONH, and n' represents an integer of 0 to 2, is preferred.

For E, (i) $CH_2CH_2$, (ii) CH=CH, (iii) $CH_2O$, (iv) $OCH_2$, (v) $CH_2NH$, (vi) $NHCH_2$, (vii) N=N, (viii) CH=N or (ix) N=CH is preferred, and in particular, (i) $CH_2CH_2$ or (ii) CH=CH is preferred.

Specifically, a 5-membered heterocyclic ring containing an oxygen atom such as 2,3-dihydrofuran, furan, 1,3-dioxole, oxazoline, isoxazole, 1,2,3-oxadiazole and oxazole, and a 6-membered heterocyclic ring containing an oxygen atom such as 2H-3,4-dihydropyran, 2H-pyran, 2,3-dehydro-1,4-dioxane and 2,3-dehydromorpholine are preferred.

More preferred is a ring represented by formula:

wherein, n represents an integer of 0 to 2, and ----- represents a single bond or double bond.

Specifically, for example, 2,3-dihydrofuran, furan, 2H-3,4-dihydropyran and 2H-pyran are used widely.

As the substituent for ring A, for example, a halogen atom (e.g., fluorine, chlorine, bromine, iodine), an optionally substituted lower alkyl group, an optionally substituted cycloalkyl group, an optionally substituted lower alkynyl group, an optionally substituted lower alkenyl group, an optionally substituted aryl group, a lower alkoxy group (e.g., $C_{1-6}$ alkoxy group such as methoxy, ethoxy, propoxy, isopropoxy, butoxy, isobutoxy, sec-butoxy, tert-butoxy, etc.), an aryloxy group (e.g., $C_{6-10}$ aryloxy group such as phenoxy, etc.), a lower alkanoyl group (e.g., formyl, $C_{1-6}$ alkyl-carbonyl group such as acetyl, propionyl, butyryl, isobutyryl, etc.), an arylcarbonyl group (e.g., $C_{6-10}$ aryl-carbonyl group such as benzoyl group, naphthoyl group; etc.), a lower alkanoyloxy group (e.g., formyloxy, $C_{1-6}$ alkyl-carbonyloxy group such as acetyloxy, propionyloxy, butyryloxy, isobutyryloxy, etc.), an arylcarbonyloxy group (e.g., $C_{6-10}$ aryl-carbonyloxy group such as benzoyloxy, naphthoyloxy, etc.), a carboxyl group, a lower alkoxycarbonyl group (e.g., $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxycarbonyl group (e.g., $C_{7-11}$ aralkyloxy-carbonyl group such as benzyloxycarbonyl, etc.), a carbamoyl group, a mono-, di- or tri-halogeno-lower alkyl group (e.g., mono-, di- or tri-halogeno-$C_{1-4}$ alkyl group such as chloromethyl, dichloromethyl, trifluoromethyl, 2,2,2-trifluoroethyl, etc.), oxo group, amidino group, imino group, amino group, a mono-lower alkylamino group (e.g., mono-$C_{1-4}$ alkylamino group such as methylamino, ethylamino, propylamino, isopropylamino, butylamino, etc.), a di-lower alkylamino group (e.g., di-$C_{1-4}$ alkylamino group such as dimethylamino, diethylamino, dipropylamino, diisopropylamino, dibutylamino, methylethylamino, etc.), a 3- to 6-membered cyclic amino group optionally containing 1 to 3 hetero atoms selected from an oxygen atom, a sulfur atom and a nitrogen atom in addition to carbon atoms and one nitrogen atom (e.g., 3- to 6-membered cyclic amino group such as aziridinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylene dioxy group (e.g., alkylene dioxy group such as methylene dioxy, ethylene dioxy, etc.), hydroxyl group, nitro group, cyano group, mecapto group, sulfo group, sulfino group, phosphono group, sulfamoyl group, mono-alkylsulfamoyl group (e.g., mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), di-alkylsulfamoyl group (e.g., di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., $C_{1-6}$ alkylthio group such as methylthio, ethylthio, propylthio, isopropylthio, butylthio, sec-butylthio, tert-butylthio, etc.), an arylthio group (e.g., $C_{6-10}$ arylthio group such as phenylthio, naphthylthio, etc.), a lower alkylsulfinyl group (e.g. $C_{1-6}$ alkylsulfinyl group such as methylsulfinyl, ethylsulfinyl, propylsulfinyl, butylsulfinyl, etc.), an arylsulfinyl group (e.g., $C_{6-10}$ arylsulfinyl group such as phenylsulfinyl, naphthylsulfinyl, etc.), a lower alkylsulfonyl group (e.g. $C_{1-6}$ alkylsulfonyl group such as methylsulfonyl, ethylsulfonyl, propylsulfonyl, butylsulfonyl, etc.), an arylsulfonyl group (e.g., $C_{6-10}$ arylsulfonyl group such as phenylsulfonyl, naphthylsulfonyl, etc.), and the like are used.

The "lower alkyl group", "lower alkenyl group", "lower alkynyl group", "lower cycloalkyl group" and "aryl group" may have 1 to 5, preferably 1 to 3, of the substituents that may be possessed by the above-mentioned "hydrocarbon group".

Examples of the substituent for ring A include a halogen atom, an optionally substituted $C_{1-6}$ alkyl group, an optionally substituted $C_{1-6}$ alkoxy group, hydroxyl group, nitro group, cyano group, an optionally substituted amino group, oxo group, and the like. The substituent of the "optionally substituted $C_{1-6}$ alkyl group", "optionally substituted $C_{1-6}$ alkoxy group" and "optionally substituted amino group" may be the substituents that may be possessed by the above-mentioned "hydrocarbon group".

The ring A may have 1 to 4, preferably 1 to 2 of the above-mentioned substituents at substitutable positions depending on the ring size, and when the number of the substituents is 2 or more, the respective substituents may be the same or different.

Examples of ring A include wherein, $R^5$ represents a hydrogen atom or 1 or 2 of the substituents represented by the above-mentioned "preferable substituent for ring A", and the other symbols are as defined above, and the like. Among them, a ring wherein $R^5$ is a hydrogen atom, hydroxyl group or an optionally substituted $C_{1-6}$ alkyl group, in particular, $R^5$ is a hydrogen atom (unsubstituted ring A), is used widely.

In the formula, n represents an integer of 0 to 2, and n is preferably an integer of 0 or 1. Particularly, preferred is the case when n is G.

In the above formula (I), ring B represents an optionally substituted benzene ring.

Examples of the substituent for ring B include the "substituent" of the above-mentioned "optionally substituted benzene ring". Inter alia, a halogen atom, hydroxyl group or an optionally substituted lower ($C_{1-6}$) alkyl group is preferred, in particular, a halogen atom, hydroxyl group or a lower ($C_{1-6}$) alkyl group (preferably methyl) is used widely. The "substituent" of the "optionally substituted lower ($C_{1-6}$) alkyl group" may be the substituents that may be possessed by the above-mentioned "hydrocarbon group".

The ring B may have 1 or 2, preferably 1 of the above-mentioned substituents at substitutable positions, and when the number of the substituents is 2, the respective substituents may be the same or different.

Preferred examples of ring B include wherein, $R^6$ represents a hydrogen atom, hydroxyl group, a halogen atom; an optionally substituted lower ($C_{1-6}$) alkyl group or an optionally substituted lower ($C_{1-6}$) alkoxy group. $R^6$ is preferably a hydrogen atom, hydroxyl group, a halogen atom or lower ($C_{1-6}$) alkyl group (preferably methyl). $R^5$ is more preferably a hydrogen atom.

In the above formula (I), m represents an integer of 1 to 4. Preferably m is an integer of 1 to 3. More preferably, m is 2 or 3, and in particular, preferred is the case when m is 2.

Preferred examples of the moiety represented by thformula wherein, $R^{4'}$ represents an optionally substituted hydrocarbon group or hydroxyl group, and the other respective symbol is as defined above.

$R^{4'}$ is preferably an optionally substituted lower ($C_{1-3}$) alkyl.

Other preferred examples of the moiety represented by the formula wherein, each symbol is as defined above. Among them, preferred is wherein, each symbol is as defined above.
Inter alia, wherein, each symbol is as defined above, is preferred. Particularly preferred is wherein, each symbol is as defined above.

In addition, preferred examples of compound (I) include a compound wherein $R^1$ is (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group or (vii) an optionally substituted 5- or 6-membered nitrogen-containing heterocyclic group, $R^2$ is a hydrogen atom or an optionally substituted lower ($C_{1-6}$) alkyl group, $R^3$ is (i) a hydrogen atom, (ii) an optionally substituted lower alkyl group or (iii) an optionally substituted aryl group, X is $CHR^4$ or $NR^4$ ($R^4$ represents a hydrogen atom or lower ($C_{1-6}$) alkyl group optionally substituted with oxo group), Y is C, CH or N (provided that, when X represents $CH_2$, Y is C or CH), ---- represents a single bond or double bond, ring A is an optionally substituted 5- to 7-membered heterocyclic ring containing an oxygen atom, ring B is an optionally substituted benzene ring, and m is 1 or 2, and the like.

More preferably, a compound wherein $R^1$ is i) $C_{1-6}$ alkyl group optionally substituted with 1 to 4 of halogen, hydroxyl group or $C_{1-6}$ alkoxy group, ii) $C_{3-6}$ cycloalkyl group, iii) $C_{2-6}$ alkenyl group, iv) $C_{6-10}$ aryl group optionally substituted with 1 to 4 of $C_{1-6}$ alkoxy group, nitro, halogeno$C_{1-6}$ alkyl-carbonylamino or halogen atom, v) mono- or di-$C_{1-6}$ alkylamino group, (vi) $C_{6-10}$ arylamino group optionally substituted with 1 to 3 of $C_{1-6}$ alkoxy group or vii) 6-membered nitrogen-containing heterocyclic group optionally substituted with 1 to 2 of $C_{7-11}$ aralkyloxy-carbonyl group,

$R^2$ is a hydrogen atom or a lower ($C_{1-6}$) alkyl group, $R^3$ is (i) a hydrogen atom, (ii) a lower ($C_{1-6}$) alkyl group or (iii) a $C_{6-14}$ aryl group,

X is $CHR^4$ or $NR^4$ ($R^4$ represents a hydrogen atom or lower ($C_{1-6}$) alkyl group optionally substituted with oxo group), Y is C, CH or N (provided that, when X represents $CH_2$, Y is C or CH), ---- represents a single bond or double bond, ring A is wherein, each symbol is as defined above,
ring B is wherein, $R^{6a}$ represents a hydrogen atom, a halogen atom or a lower ($C_{1-6}$) alkyl group, and
m is 1 or 2, and the like.

Among these, a compound represented by formula wherein, $R^{1b}$ represents a $C_{1-6}$ alkyl group optionally having a hydroxyl group, $R^{6b}$ represents a hydrogen atom or a halogen atom, n represents 0 or 1, represents a single bond or double bond, and when $X^b$ represents $CH_2$, represents a single bond or double bond and when $X^b$ represents NH, represents a single bond, or a salt thereof is preferred.

In addition, a compound represented by formula wherein, $R^{1b}$ represents a $C_{1-6}$ alkyl group optionally having a hydroxyl group, X' represents $CH_2$, NH or NCHO, $R^{3a}$ represents a hydrogen atom or phenyl group, ---- represents a single bond or double bond, $E^a$ represents $CH_2CH_2$, CH=CH, $CH_2O$, CH=N, CONH or $CH_2NH$, $n^a$ represents 0 or 1, ring A" represents an oxygen-containing 5- or 6-membered heterocyclic ring which may have 1 or 2 of $C_{1-6}$ alkyl group optionally substituted with a hydroxyl group, and ring B' represents a benzene ring optionally substituted with a halogen atom, or a salt thereof is also preferred. Among these, a compound wherein, when X' is $CH_2$ or NCHO, ---- is a single bond or double bond and when X' is NH, ---- is a single bond, or a salt thereof is also preferred.

Preferable examples of compound (I) include N-[2-(1,6,7,8-tetrahydro-2H-indeno[5,4-b]furan-8-yl)ethyl]acetamide, N-[2-(1,6,7,8-tetrahydro-2H-indeno[5,4-b]furan-8-yl)ethyl]butyramide, N-[2-(1,6,7,8-tetrahydro-2H-indeno[5,4-b]furan-8-yl)ethyl]propionamide, N-[2-(3,7,8,9-tetrahydropyrano[3,2-e]indol-1-yl)ethyl]propionamide, N-[2-(5-fluoro-3,7,8,9-tetrahydrocycopenta[f][1]benzopyran-9-yl)ethyl]propionamide, N-[2-(3,7,8,9-tetrahydropyrano[3,2-e]indol-1-yl)ethyl]butyllamide, N-[2-(1,2,3,7,8,9-hexahydropyrano[3,2-e]indol-1-yl)ethyl]propionamide, N-[2-(1,2,3,7,8,9-hexahydropyrano[3,2-e]indol-1-yl)ethyl]butyllamide, N-[2-(4-fluoro-1,6,7,8-tetrahydro-2H-indeno[5,4-b]furan-8-yl)ethyl]butyllamide, N-[2-(4-fluoro-1,6,7,8-tetrahydro-2H-indeno[5,4-b]furan-8-yl)ethyl]propionamide, (S)—N-[2-(1,6,7,8-tetrahydro-2H-indeno[5,4-b]furan-8-yl)ethyl]propionamide, (R)—N-[2-(1,6,7,8-tetrahydro-2H-indeno[5,4-b]furan-8-yl)ethyl]propionamide, N-[2-(1,6,7,8-tetrahydro-2H-indeno[5,4-b]furan-8-yl)ethyl]butyllamide, N-[2-(1,6-dihydro-2H-indeno[5,4-b]furan-8-yl)ethyl]acetamide, N-[2-(1,6-dihydro-2H-indeno[5,4-b]furan-8-yl)ethyl]propionamide, N-[2-(1,6-dihydro-2H-indeno[5,4-b]furan-8-yl)ethyl]butyllamide, N-[2-(7,8-dihydro-6H-indeno[4,5-d]-1,3-dioxol-8-yl)ethyl]propionamide, N-[2-(7,8-dihydro-6H-indeno[4,5-d]-1,3-dioxol-8-yl)ethyl]butyllamide, N-[2-(2,3,8,9-tetrahydro-7H-indeno[4,5-b]-1,4-dioxin-9-yl)ethyl]propionamide, N-[2-(2,3,8,9-tetrahydro-7H-indeno[4,5-b]-1,4-dioxin-9-yl)ethyl]butyllamide, N-[2-(1,6,7,8-tetrahydro-2H-furo[3,2-e]indol-8-yl)ethyl]propionamide, N-[2-(1,6,7,8-tetrahydro-2H-furo[3,2-e]indol-8-yl)ethyl]butyllamide, N-[2-(7-phenyl-1,6-dihydro-2H-indeno[5,4-b]furan-8-yl)ethyl]propionamide, N-[2-(7-phenyl-1,6-dihydro-2H-indeno[5,4-b]furan-8-yl)ethyl]butyllamide, (2S)-2-hydroxy-N-2-[(8S)-1,6,7,8-tetrahydro-2H-indeno[5,4-b]furan-8-ylethyl]propionamide, N-[2-[(8R)-6-oxo-1,6,7,8-tetrahydro-2H-indeno[5,4-b]furan-8-yl)ethyl]propionamide, 2-hydroxy-N-[2-[(8R)-6-oxo-1,6,7,8-tetrahydro-2H-indeno[5,4-b]furan-8-yl)ethyl]propionamide, N-[2-[(8R)-1-hydroxy-1,6,7,8-tetrahydro-2H-indeno[5,4-b]furan-8-yl)ethyl]propionamide, N-[2-[(8R)-1-hydroxy-6-oxo-1,6,7,8-tetrahydro-2H-indeno[5,4-b]furan-8-yl)ethyl]propionamide, N-[2-[(8R)-6-hydroxy-1,6,7,8-tetrahydro-2H-indeno[5,4-b]furan-8-yl)ethyl]propionamide, 2-hydroxy-N-[2-[(8R)-6-hydroxy-1,6,7,8-tetrahydro-2H-indeno[5,4-b]furan-8-yl)ethyl]propionamide, N-[2-[(8S)-4-hydroxy-1,6,7,8-tetrahydro-2H-indeno[5,4-b]furan-8-yl)ethyl]propionamide, and the like.

More preferably, compound (I) is N-[2-[(1,6,7,8-tetrahydro-2H-indeno[5,4-b]furan-8-yl)ethyl]acetamide, N-[2-[(1,6,7,8-tetrahydro-2H-indeno[5,4-b]furan-8-yl)ethyl]propionamide, N-[2-(5-fluoro-3,7,8,9-tetrahydrocycopenta[f][1]benzopyran-9-yl)ethyl]propionamide, N-[2-(5-fluoro-1,2,3,7,8,9-hexahydrocycopenta[f][1]benzopyran-9-yl)ethyl]propionamide, (S)—N-[2-[(1,6,7,8-tetrahydro-2H-indeno[5,4-b]furan-8-yl)ethyl]propionamide, (R)—N-[2-(1,6,7,8-tetrahydro-2H-indeno[5,4-b]furan-8-yl)ethyl]propionamide, N-[2-(1,6,7,8-tetrahydro-2H-indeno[5,4-b]furan-8-yl)ethyl]butyllamide, N-[2-(1,6-dihydro-2H-indeno[5,4-b]furan-8-yl)ethyl]acetamide. N-[2-(1,6-dihydro-2H-indeno[5,4-b]furan-8-yl)ethyl]propionamide, N-[2-(1,6-dihydro-2H-indeno[5,4-b]furan-8-yl)ethyl]butyllamide, N-[2-(1,6,7,8-tetrahydro-2H-furo[3,2-e]indol-8-yl)ethyl]propionamide, N-[2-(1,6,7,8-tetrahydro-2H-furo[3,2-e]indol-8-yl)ethyl]butyllamide, N-[2-(7-phenyl-1,6-dihydro-2H-indeno[5,4-b]furan-8-yl)ethyl]propionamide, N-[2-(7-phenyl-1,6-dihydro-2H-indeno[5,4-b]furan-8-yl)ethyl]butyllamide, (2S)-2-hydroxy-N-[2-[(8S)-1,6,7,8-tetrahydro-2H-indeno[5,4-b]furan-8-yl)ethyl]propionamide, or N-[2-[(8R)-6-oxo-1,6,7,8-tetrahydro-2H-indeno[5,4-b]furan-8-yl)ethyl]propionamide.

Particularly preferably, compound (I) is (S)—N-[2-(1,6,7,8-tetrahydro-2H-indeno[5,4-b]furan-8-yl)ethyl]propionamide, N-[2-(1,6,7,8-tetrahydro-2H-furo[3,2-e]indol-8-yl)ethyl]propionamide, N-[2-(1,6,7,8-tetrahydro-2H-furo[3,2-e]indol-8-yl)ethyl]butyllamide, N-[2-(7-phenyl-1,6-dihydro-2H-indeno[5,4-b]furan-8-yl)ethyl]propionamide, N-[2-(7-phenyl-1,6-dihydro-2H-indeno[5,4-b]furan-8-yl)ethyl]butyllamide, (2S)-2-hydroxy-N-[2-[(8S)-1,6,7,8-tetrahydro-2H-indeno[5,4-b]furan-8-yl)ethyl]propionamide, or N-[2-[(8R)-6-oxo-1,6,7,8-tetrahydro-2H-indeno[5,4-b]furan-8-yl)ethyl]propionamide.

As a salt of compound represented by formula (I) of the present invention, for example, a pharmacologically acceptable salt is used. Examples of the salt include salts with inorganic base, salts with organic base, salts with inorganic acid, salts with organic acid, salts with basic or acidic amino acid, and the like. Preferred examples of the salts with inorganic base include alkali metal salts such as sodium salt and potassium salt, alkaline earth metal salts such as calcium salt and magnesium salt, and aluminum salt, ammonium salt, and the like. Preferred examples of the salts with organic base include salts with trimethylamine, triethylamine, pyridine, picoline, 2,6-lutidine, ethanolamine, diethanolamine, triethanolamine, cyclohexylamine, dicyclohexylamine, N,N' dibenzylethylenediamine, and the like. Preferred examples of the salts with inorganic acid include salts with hydrochloric acid, hydrobromic acid, nitric acid, sulfuric acid, phosphoric acid, and the like. Preferred examples of the salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like. Preferred examples of the salts with basic amino acid include salts with arginine, lysine, ornithine, and the like, and preferred examples of a salt with acidic amino acid include salts with asparaginic acid, glutamic acid, and the like.

Among these, a pharmaceutically acceptable salt is preferred, and as examples thereof, in case that the compound represented by formula (I) has a basic functional group within the molecule, a salt with inorganic acid such as hydrochloric acid, hydrobromic acid, nitric acid, sulfuric acid, phosphoric acid, and the like and a salt with organic acid such as acetic acid, phthalic acid, fumaric acid, tartaric acid, maleic acid, citric acid, succinic acid, methanesulfonic acid, p-toluenesulfonic acid, and the like are exemplified, furthermore in case that the compound represented by formula (I) has a acidic functional group, alkali metal salts such as sodium salt and potassium salt, alkaline earth metal salts such as calcium salt and magnesium salt, ammonium salt, and the like are exemplified.

In addition, the compound represented by formula (I) of the present invention may be a hydrate or non-hydrate.

As the compound represented by formula (I) or a salt thereof, particularly preferred is (S)—N-[2-(1,6,7,8-tetrahydro-2H-indeno[5,4-b]furan-8-yl)ethyl]propionamide (generic name: Ramelteon) (hereinafter, sometimes referred to as compound A).

The compound represented by formula (I) or a salt thereof is a known therapeutic agent for sleep disorder disclosed in U.S. Pat. No. 6,034,239 and the like, and can be produced by a known method such as the method described in said reference.

In addition, the compound represented by formula (I) of the present invention can be synthesized according to the production method described in JP 10-287665A or an analogous method thereto, and if desired, a combination of the method and a conventional oxidation method.

The compound represented by formula (I) or a salt thereof can be used for a prevention or treatment of irritable bowel syndrome, and for a prevention or treatment of abdominal pain associated with irritable bowel syndrome and bowel movement disorder associated with irritable bowel syndrome.

In addition, since the compound represented by formula (I) or a salt thereof has an antianxiety action, it can be used as a prophylactic or therapeutic agent for irritable bowel syndrome known for involvement of mental stress.

The compound represented by formula (I) or a salt thereof can also be used for a prevention or treatment of inflammatory bowel disease (IBD), functional dyspepsia and gastroesophageal reflux disease (GERD).

Further, since the compound represented by formula (I) or a salt thereof is extremely low toxic, it can be used for a prevention or treatment of irritable bowel syndrome, and for a prevention or treatment of abdominal pain associated with irritable bowel syndrome and bowel movement disorder associated with irritable bowel syndrome by combining with one or more of other prophylactic or therapeutic agents for irritable bowel syndrome, and thus the side effects caused by the other prophylactic or therapeutic agents for irritable bowel syndrome can be reduced by lowering the dose of such drugs.

Examples of such prophylactic or therapeutic agents for irritable bowel syndrome include alosetron, tegaserod, polycarbophil calcium and trimebutine.

In addition, since the compound represented by formula (I) or a salt thereof is extremely low toxic, it may be used in combination with one or more of other gastrointestinal motilitystimulant, sedative drug, antidepressant, and/or antianxiety drug.

Examples of the "gastrointestinal motility stimulant" include domperidone, metoclopramide, mosapride, itopride, tegaserod, and the like.

Examples of the "antidepressant" include tricyclic antidepressants [e.g, Doxepin, Imipramine hydrochloride, Amitriptyline, Clomipramine], tetracyclic antidepressants [e.g., Mianserine, Setiptiline, Maprotiline], SSRI [e.g., Fluoxetine, Sertraline, Paroxetine, Citalopram, Escitalopram, Fluvoxamine], SNRI [e.g., Milnacipran, Duloxetine, Venlafaxine, Trazodone, Nefazodone, Minaprine, Mirtazapine], triple uptake inhibitors [e.g., DOV-216303, NS-2359], NK1 receptor antagonist, and drugs having both melatonin receptor agonistic action and serotonin 2 receptor antagonistic action [e.g., Agomelatine], and the like.

Examples of the "antianxiety drug" include GABA-A agonistic antianxieties [e.g., Diazepam, Flutazolam, Lorazepam, Ethyl loflazepate, Flutoprazepam, Mexazolam, Clotiazepam, Etizolam, Hydroxyzine, Alprazolam, Fludiazepam, Chlordiazepoxide, Cloxazolam, Clorazepate, Oxazolam], serotonin antianxieties [e.g., Buspirone, Tandospirone], and the like.

In addition, the compound represented by formula or a salt thereof may be used in combination with the following drugs.
(a) 5-HT$_3$ receptor antagonist: for example, dolasetron, palonosetron, alosetron, azasetron, ramosetron, mitrazapine, granisetron, tropisetron, E-3620, ondansetron and indisetron;
(b) 5-HT$_4$ receptor agonist: for example, tegaserod, mosapride, cinitapride and oxtriptane;
(c) laxative agent: for example, Trifyba (trade name), Fybogel (trade name), Konsyl (trade name), Isogel (trade name), Regulan (trade name), Celevac (trade name) and Normacol (trade name); Amitiza (trade name)
(d) dopamine receptor antagonist: for example, metoclopramide, domperidone and levosulpiride
(e) tachykinin (NK) receptor antagonist (in particular, NK-3, NK-2 and NK-1 antagonist): for example, nepadutant, saredutant, talnetant, (αR,9R)-7-[3,5-bis(trifluoromethyl) benzyl]-8,9,10,11-tetrahydro-9-methyl-5-(4-methylphenyl)-7H-[1,4]diazocino[2,1-g][1,7]naphthyridin-6,13-dione, 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazole-3-one (MK-869), lanepitant, dapitant and 3-[[2-methoxy-5-(trifluoromethoxy)phenyl] methylamino]-2-phenyl-piperidine (2S,3S);
(f) vanilloid receptor 1 antagonist: for example, AMG-517 and GW-705498;
(g) ghrelin receptor agonist: for example, capromorelin and TZP-101;
(h) AchE release stimulant: for example, Z-338 and KW-5092;
(i) CRF antagonist: for example, CP-316311 and TS-041;
(j) vasopressin antagonist: for example, SSR149415 and SRX251;
(k) glucocorticoid receptor antagonist: for example, mifepristone and Org-34517;
(l) cannabinoid receptor agonist: for example, Δ9-THC, CP-55940, WIN-55212-2, HU-210;
(m) FAAH inhibitor: for example, OL-135, LY2077855 and URB-597

These drugs to be used in combination (concomitant drugs) may be a free form or a pharmaceutically acceptable salt.

In this case, timing of administration of the prophylactic or therapeutic agent for irritable bowel syndrome of the present invention and the concomitant drugs is not limited, and these can be administered to the subjects simultaneously or at different times.

Examples of administration forms include
(1) administration of a single preparation obtained by formulating the melatonin agonist to be used in the present invention and concomitant drug simultaneously,
(2) simultaneous administration via the same administration route of two preparations obtained by formulating the melatonin agonist to be used in the present invention and concomitant drug respectively,
(3) separate administration at an interval via the same administration route of two preparations obtained by formulating the melatonin agonist to be used in the present invention and concomitant drug respectively,
(4) simultaneous administration via different routes of two preparations obtained by formulating the melatonin agonist to be used in the present invention and concomitant drug respectively,
(5)-separate administration at an interval via different routes of two preparations obtained by formulating the melatonin agonist to be used in the present invention and concomitant drug respectively (for example, administration in the order of compound of the present invention concomitant drug, or in the inverse order) and the like.

Dosage of concomitant drug can be appropriately selected on the basis of the clinically used dosage. In addition, the combination ratio of the compound of the present invention and concomitant drug can be appropriately selected depending on a subject to be administered, an administration route, targeted diseases, symptoms, combinations thereof or the like. For example, when the subject to be administered is a human, the concomitant drug may be used with an amount of 0.01 to 100 parts by weight based on 1 part by weight of compound A. In case of other melatonin agonist, dosage of the concomitant drug can be decided according to compound A.

The melatonin agonist to be used in the present invention can be safely administered orally or parenterally (e.g. topically, rectally, intravenously etc.) as it is or as a pharmaceutical composition mixed with pharmacologically acceptable carriers according to a conventional method (e.g., method described in Japanese Pharmacopoeia, etc.), such as tablets (including sugar-coated tablets, film-coated tablets), powders, granules, capsules, solutions, emulsions, suspensions, injectables, suppositories, sustained-release agents (controlled-release preparation), adhesive preparations, and the like.

The content of compound A in the pharmaceutical composition is usually about 0.01 to 100% by weight based on a total weight of the composition. The content of other melatonin agonist can be decided according to compound A.

The dose of the melatonin agonist to be used in the present invention differs depending on melatonin agonist to be used, administration subject, administration route, and the like. For example, when compound A is administered to an adult as an oral agent, the dose is about 0.0005 to 2 mg/kg body weight, preferably about 0.001 to 1 mg/kg body weight, more preferably about 0.01 to 1 mg/kg body weight as an active ingredient. The pharmaceutical composition may be administered once to several times in divided doses per day. The dose of other melatonin agonist can be decided according to compound A.

EXAMPLES

The present invention will be described in detail through the following Preparation Example and Test Examples. However, the present invention is not limited by these examples.

Preparation Example 1

Compound A (160 g), lactose (4064 g), and corn starch (640 g) are mixed uniformly in a fluidized bed granulation dryer, and the mixture is granulated with spraying a solution of hydroxypropyl cellulose (160 g) in water in the dryer, followed by drying in said drier. The resulting granulated material is crushed by 1.5 mmϕ punching screen using a power mill apparatus to obtain uniform granules. To the uniform granules (3894 g) are added corn starch (124 g) and magnesium stearate (12.4 g), and the mixture is mixed to give granules for tableting. These granules are tableted in a weight of 130 mg per tablet with a 7.0 mmϕ die using a tableting machine to prepare bare tablets. The obtained bare tablets are sprayed with a solution of hydroxypropylmethylcellulose 2910 and copolividone wherein titanium oxide and yellow ferric oxide are dispersed, in a film coating machine, to give about 25000 tablets which are film-coated tablets each containing 4 mg of compound A per tablet and having a prescription shown in Table 1.

TABLE 1

| Composition | Blending Quantity (mg) |
| --- | --- |
| Compound A | 4.0 |
| Lactose | 101.6 |
| Corn Starch | 20.0 |
| Hydroxypropyl Cellulose | 4.0 |
| Magnesium stearate | 0.4 |
| Bare Tablet | 130.0 |
| Hydroxypropylmethylcellulose 2910 | 3.74 |
| Copolividone | 0.75 |
| Titanium Oxide | 0.5 |
| Yellow Ferric Oxide | 0.01 |
| Total | 135.0 |

Test Example 1

Action of Compound A on Viscerosenditivity

Method

For the experiment, 7 to 8 week-old male SD rats (CREA Japan, Inc.) were used. Under ether anesthesia, the rats were sutured with a force transducer (F12-IS-SL, Star Medical Inc.) on the abdominal oblique muscle, and used for the experiment after waiting at least one day or more postoperatively for recovery of the animals.

After fasting for 18 hours, 1% acetic acid was instilled into the colon to produce a hypersensitive condition. One hour after the instillation of acetic acid, a balloon was inserted into the colon, fixed, and colonic distension stimulus was loaded for 10 minutes by inflating the balloon. The colonic distension stimulus was loaded two times before and after administration of compound A, and the observed contraction number of the abdominal oblique muscle was counted. The result was expressed as inhibition percent. Determination of the abdominal muscle contraction was conducted with the naked eye and waveform of force transducer.

Compound A was suspended in a 0.5% methylcellulose, and administered orally with a volume of 4 mL/kg 30 minutes before the second colonic distension stimulus (0.3, 3 and 30 mg/kg).

Result

Figure 1:
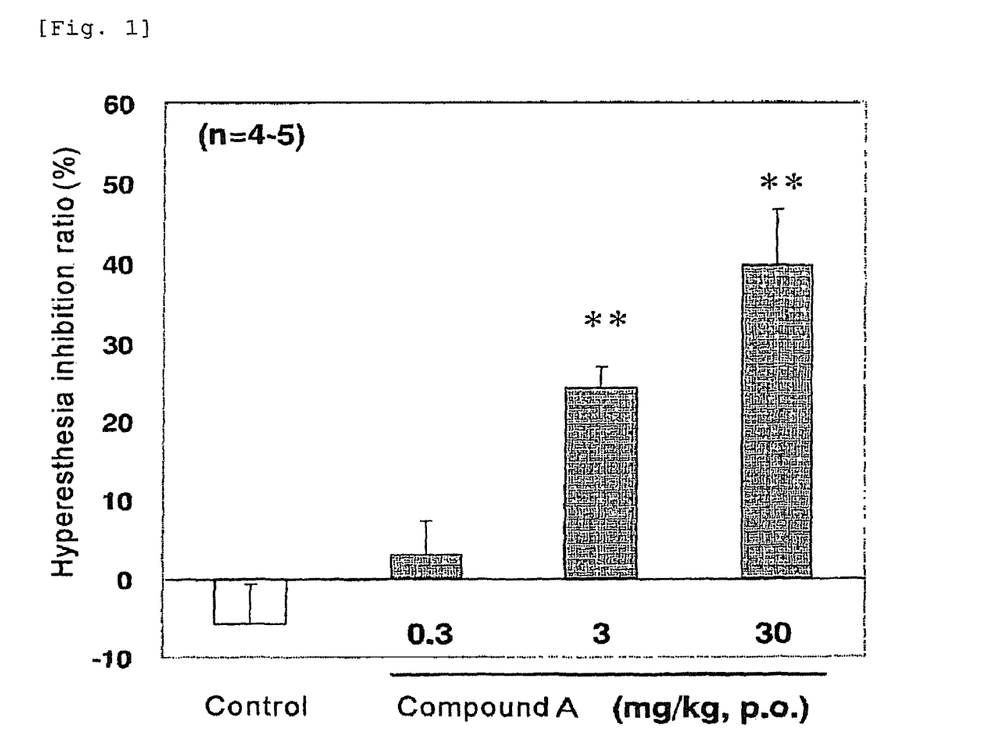
FIG. 1 is a graph showing viscerosensory response test for compound A.

The result was shown in FIG. 1 (n=4 to 5, **$P \leq 0.025$ vs. control group, Williams test). As is clear from this figure, compound A shows a dose-dependent significant inhibition action on viscerosensory response.

Test Example 2

Method

For the experiment, 10 week-old male Wistar rats (SLC) were used. Compound A (0.3, 3, 10 and 30 mg/kg) or a vehicle (control group, 0.5% methylcellulose) was administered orally with a dose of 4 ml/kg, and after 15 minutes, a restraint stress was loaded. Fecal pellets were retrieved 2 hours after the beginning of the restraint stress loading, and the number of feces was counted. In addition, as for normal group, rats were left in their individual cages without any after administration of vehicle, and the number of feces for 2 hours was counted.

Further, a study on normal defecation was also conducted. Until the day before the experiment, two rats were kept in a cage and accustomed to the measuring condition. On the day of experiment, compound A or vehicle (control group, 0.5% methylcellulose) was administered orally with a dose of 4 ml/kg, and after 15 minutes, the measurement of defecation was commenced. The number of feces was counted two hours after the initiation of measurement, and the result was expressed by the number of feces per two rats.

Result

Figure 2:
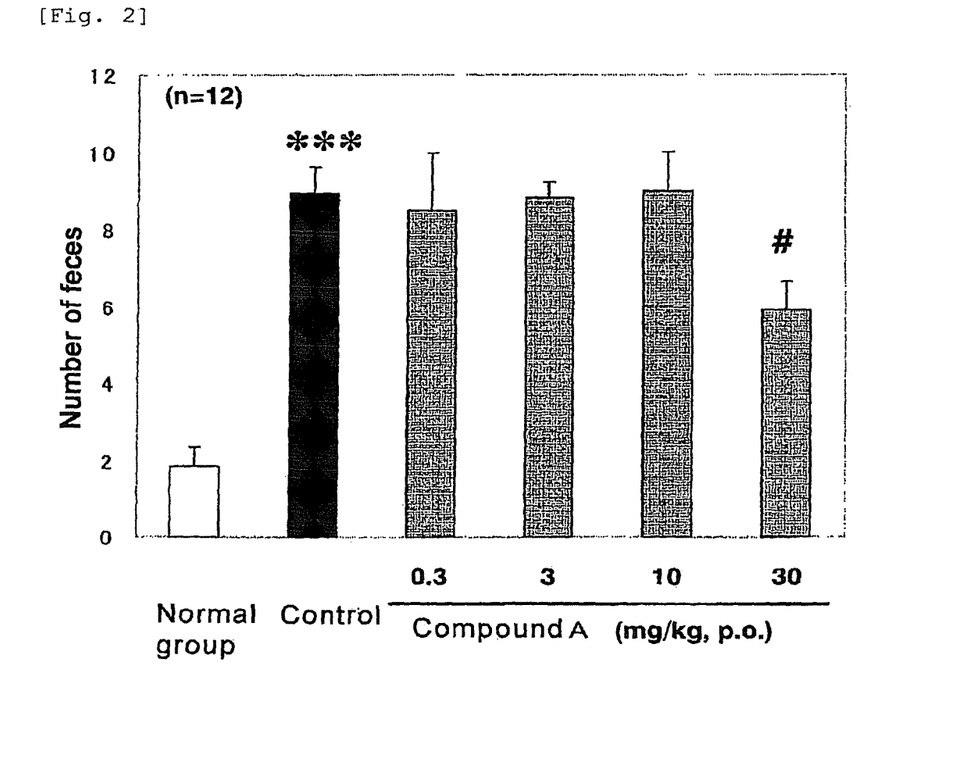
FIG. 2 is a graph showing restraint stress-induced defecation test for compound A.
Figure 3:
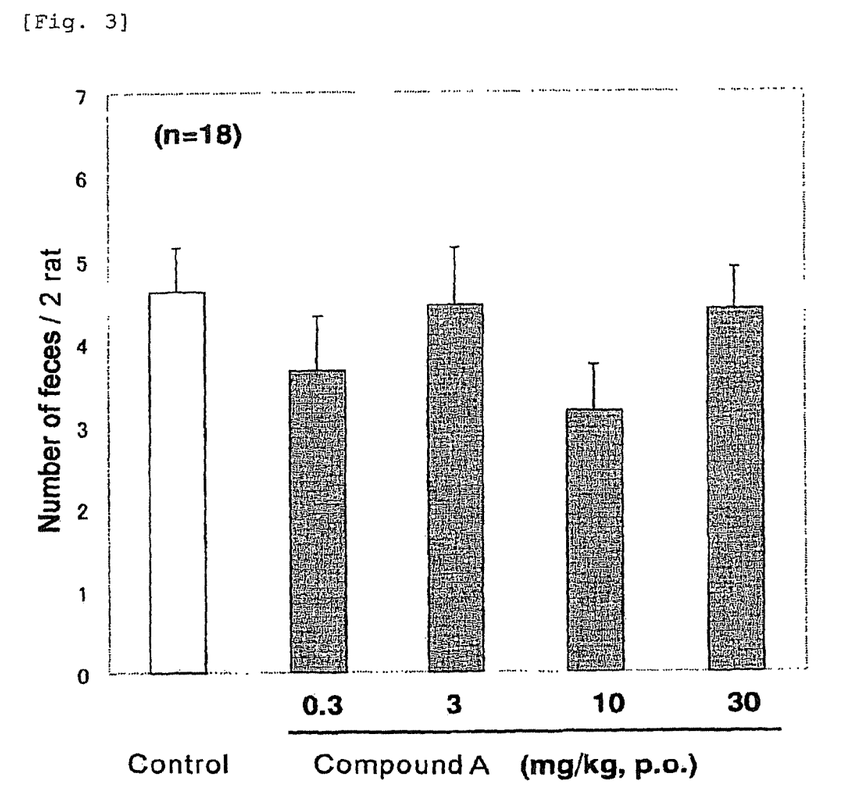
FIG. 3 is a graph showing normal defecation test for compound A.

The result was shown in FIG. 2 (*$P 0.001$ vs. normal group (Student's t-test), #$P<0.025$ vs. control group (Parametric Williams test) and FIG. 3. As seen from FIG. 2, compound A inhibited significantly the restraint stress-induced defecation in the 30 mg/kg administered group. On the other hand, as is clear from FIG. 3**, normal defecation was not inhibited even in the administration of 30 mg/kg.

Test Example 3

Comparison Example

Method

Experiment was carried out according to Test Example 2, wherein melatonin (10 and 30 mg/kg) instead of compound A was administered orally.

Result

Figure 4:
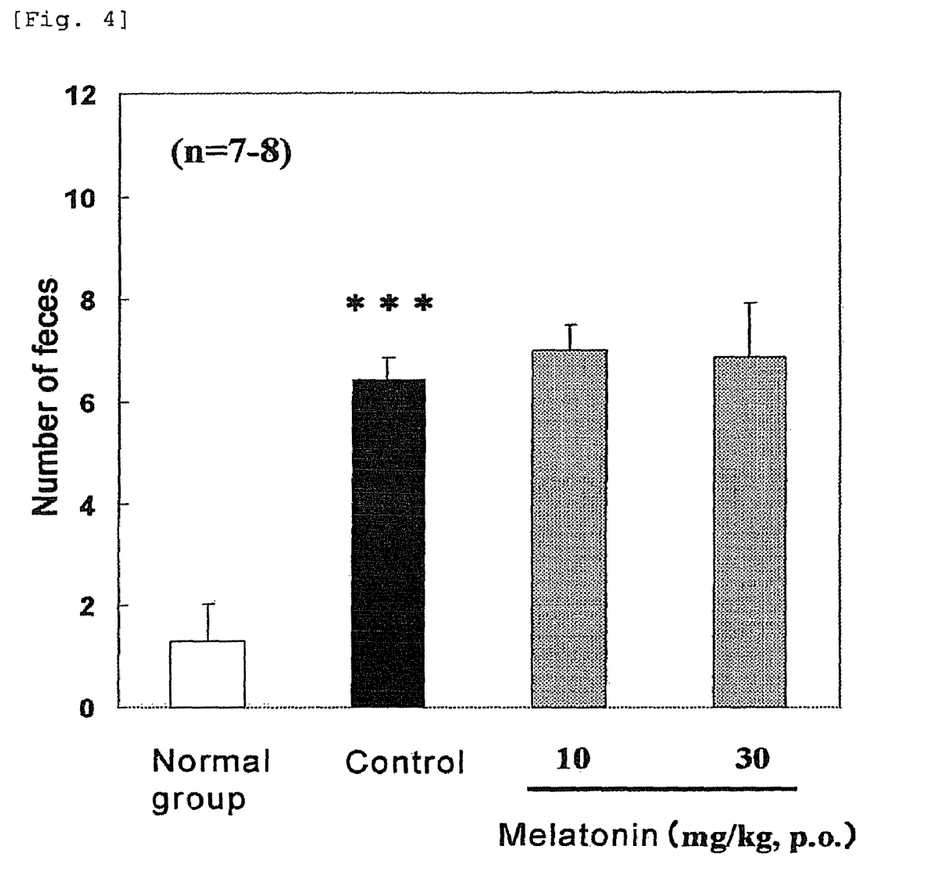
FIG. 4 is a graph showing a restraint stress-induced defecation test for melatonin.

The result was shown in FIG. 4 (*P≦0.001 vs. normal group (Student's t-test)). As shown in FIG. 4**, melatonin did not inhibit the restraint stress-induced defecation in the 10 and 30 mg/kg administration.

INDUSTRIAL APPLICABILITY

According to the present invention, a prophylactic or therapeutic agent for irritable bowel syndrome is provided.

The invention claimed is:

1. A method for treatment of irritable bowel syndrome, which comprises administering an effective amount of a compound represented by formula (I):

wherein, $R^1$ represents an optionally substituted hydrocarbon group, an optionally substituted amino group or an optionally substituted heterocyclic group,
$R^2$ represents a hydrogen atom or an optionally substituted hydrocarbon group,
$R^3$ represents a hydrogen atom, an optionally substituted hydrocarbon group or an optionally substituted heterocyclic group,
X represents $CHR^4$, $NR^4$, CO, O or S wherein, $R^4$ represents a hydrogen atom, an optionally substituted hydrocarbon group or hydroxyl group,
Y represents C, CH or N,
---- represents a single bond or double bond,
ring A represents an optionally substituted 5- to 7-membered heterocyclic ring containing an oxygen atom,
ring B represents an optionally substituted benzene ring, and m represents an integer of 1 to 4, or a salt thereof, wherein the compound represented by formula (I) or a salt thereof is (S)—N-[2-(1,6,7,8-tetrahydro-2H-indeno[5,4-b]furan-8-yl)ethyl]propionamide.

* * * * *